US009914700B2

(12) United States Patent
Tenn, III

(10) Patent No.: US 9,914,700 B2
(45) Date of Patent: Mar. 13, 2018

(54) ENHANCED EXTRACTION OF IMPURITIES FROM MIXTURE COMPRISING NITRILES

(71) Applicant: INVISTA NORTH AMERICA S.A R.L., Wilmington, DE (US)

(72) Inventor: William J. Tenn, III, Beaumont, TX (US)

(73) Assignee: INVISTA NORTH AMERICA S.A R.L., Wilmington, DE (US)

( * ) Notice: Subject to any disclaimer, the term of this patent is extended or adjusted under 35 U.S.C. 154(b) by 0 days.

(21) Appl. No.: 15/320,898

(22) PCT Filed: Jun. 25, 2015

(86) PCT No.: PCT/US2015/037635
§ 371 (c)(1),
(2) Date: Dec. 21, 2016

(87) PCT Pub. No.: WO2015/200597
PCT Pub. Date: Dec. 30, 2015

(65) Prior Publication Data
US 2017/0197909 A1 Jul. 13, 2017

Related U.S. Application Data

(60) Provisional application No. 62/018,117, filed on Jun. 27, 2014.

(51) Int. Cl.
| | |
|---|---|
| *C07C 253/34* | (2006.01) |
| *B01D 3/12* | (2006.01) |
| *B01J 31/18* | (2006.01) |
| *B01J 31/40* | (2006.01) |
| *B01J 38/56* | (2006.01) |
| *B01J 38/04* | (2006.01) |
| *B01D 11/04* | (2006.01) |
| *B01D 11/00* | (2006.01) |

(52) U.S. Cl.
CPC .............. *C07C 253/34* (2013.01); *B01D 3/12* (2013.01); *B01D 11/0461* (2013.01); *B01D 11/0492* (2013.01); *B01J 31/185* (2013.01); *B01J 31/40* (2013.01); *B01J 38/04* (2013.01); *B01J 38/56* (2013.01); *B01D 2011/002* (2013.01); *B01J 2231/322* (2013.01); *B01J 2531/002* (2013.01)

(58) Field of Classification Search
CPC ................................. C07C 253/34; B01D 3/12
See application file for complete search history.

(56) References Cited

U.S. PATENT DOCUMENTS

| | | | |
|---|---|---|---|
| 3,496,215 A | 2/1970 | Drinkard et al. | |
| 3,496,217 A | 2/1970 | Drinkard, Jr. et al. | |
| 3,496,218 A | 2/1970 | Drinkard, Jr. | |
| 3,773,809 A | 11/1973 | Walter | |
| 4,082,811 A | 4/1978 | Shook, Jr. | |
| 4,339,395 A | 7/1982 | Barnette et al. | |
| 4,988,652 A * | 1/1991 | Shima ................. | B01J 31/0231 423/140 |
| 5,105,015 A * | 4/1992 | Lin ....................... | C07C 209/48 564/491 |
| 5,512,695 A | 4/1996 | Kreutzer et al. | |
| 5,512,696 A | 4/1996 | Kreuter et al. | |
| 5,523,453 A | 6/1996 | Breikss | |
| 5,543,536 A | 8/1996 | Tam | |
| 5,663,369 A | 9/1997 | Kreutzer et al. | |
| 5,688,986 A | 11/1997 | Tam et al. | |
| 5,693,843 A | 12/1997 | Breikss et al. | |
| 5,723,641 A | 3/1998 | Tam et al. | |
| 5,847,101 A | 12/1998 | Okayama et al. | |
| 5,959,135 A | 9/1999 | Garner et al. | |
| 6,120,700 A | 9/2000 | Foo et al. | |
| 6,171,996 B1 | 1/2001 | Garner et al. | |
| 6,171,997 B1 | 1/2001 | Foo et al. | |
| 6,399,534 B2 | 6/2002 | Bunel et al. | |
| 6,924,345 B2 | 8/2005 | Gagne et al. | |
| 6,936,171 B2 | 8/2005 | Jackson et al. | |
| 7,935,229 B2 | 5/2011 | Deckert et al. | |
| 9,676,800 B2 * | 6/2017 | Tenn, III .............. | B01J 31/4053 |
| 2013/0211126 A1 | 8/2013 | Moerbe et al. | |

FOREIGN PATENT DOCUMENTS

| | | |
|---|---|---|
| WO | 2001/036429 A1 | 5/2001 |
| WO | 2005/073241 A1 | 8/2005 |
| WO | 2013/095853 A1 | 6/2013 |
| WO | 2014/205337 A1 | 12/2014 |
| WO | 2015/200597 A1 | 12/2015 |

OTHER PUBLICATIONS

International Search Report and Written Opinion Received for PCT Application No. PCT/US2015/037635, dated Oct. 2, 2015, 12 pages.
International Preliminary Report on Patentability Received for PCT Patent Application No. PCT/US2015/037635, dated Jan. 5, 2017, 10 pages.

* cited by examiner

*Primary Examiner* — Golam M Shameem
(74) *Attorney, Agent, or Firm* — Robert B. Furr, Jr.; Edward F. Kenehan, Jr.

(57) ABSTRACT

Disclosed herein are methods for recovering phosphorus-containing ligand from mixtures comprising organic mononitriles and organic dinitriles, using liquid-liquid extraction. Also disclosed are treatments to enhance extractability of the phosphorus-containing ligand.

15 Claims, 3 Drawing Sheets

ENHANCED EXTRACTION OF IMPURITIES FROM MIXTURE COMPRISING NITRILES

FIELD OF THE INVENTION

The invention relates to recovery of catalyst and ligand from a hydrocyanation reaction product mixture comprising organic dinitriles using liquid-liquid extraction.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phosphite, phosphinite and phosphorite ligands can be used to form nickel-based catalysts to perform such hydrocyanation reactions.

U.S. Pat. No. 3,773,809 describes a process for the recovery of Ni complexes of organic phosphites from a product fluid containing organic nitriles produced by hydrocyanating an ethylenically unsaturated organic mononitrile such as 3-pentenenitrile through extraction of the product fluid with a paraffin or cycloparaffin hydrocarbon solvent. Similarly, U.S. Pat. No. 6,936,171 to Jackson and McKinney discloses a process for recovering diphosphite-containing compounds from streams containing dinitriles.

U.S. Pat. No. 4,339,395 describes the formation of an interfacial rag layer during extended periods of continuous extraction of certain phosphite ligands. The '395 patent notes that the interfacial rag hinders, if not halts, the phase separation. Because the process is operated continuously, the rag must be removed continuously from the interface as it accumulates to avoid interrupting operation. To solve this problem for the disclosed components, the '395 patent discloses the addition of minor amounts of substantially water-free ammonia.

U.S. Pat. No. 7,935,229 describes a process for extractively removing heterogeneously dissolved catalyst from a reaction effluent of a hydrocyanation of unsaturated mononitriles to dinitriles with a hydrocarbon. The catalyst comprises a ligand which may be a monophosphite, a diphosphite, a monophosphonite or a diphosphonite. Ammonia or an amine may be added to a mixture of liquid phases before phase separation takes place.

A mixing section of a liquid-liquid extractor forms an intimate mixture of unseparated light and heavy phase. This intimate mixture comprises an emulsion phase. The emulsion phase may or may not comprise particulate solid material. This emulsion phase separates into a light phase and a heavy phase in a settling section. Accordingly, a settling section will contain at least some emulsion phase located between the upper light phase and the lower heavy phase. This emulsion phase tends to reduce in size over time. However, in some instances settling takes longer than desired or the emulsion phase never fully separates into a light phase and a heavy phase.

Addition of Lewis base, such as water, ammonia or amine, to the feed to a liquid-liquid extractor may result in enhanced settling of the emulsion phase. For example, this addition may result in the reduction of the size of the emulsion phase in the settling section, wherein the size of the emulsion phase is based upon the size of the emulsion phase in the absence of addition of Lewis base. Enhanced settling in the settling section may also be measured as an increased rate of settling, based upon the rate of settling in the absence of addition of Lewis base.

Another problem, which may be solved by addition of Lewis base, is formation of rag and build-up of a rag layer the settling section. Rag formation is discussed in U.S. Pat. No. 4,339,395 and U.S. Pat. No. 7,935,229. Rag comprises particulate solid material, and may be considered to be a form of an emulsion phase, which is particularly stable in the sense that it does not dissipate in a practical amount of time for conducting an extraction process. Rag may form in the mixing section or the settling section of an extraction stage. In the settling section, the rag forms a layer between the heavy phase and the light phase. The formation of a rag layer in the settling section inhibits proper settling of the heavy phase and the light phase. The formation of a rag layer may also inhibit the extraction of phosphorus-containing ligand from the heavy phase into the light phase. In a worst case scenario, rag can build up to the extent of completely filling a separation section, necessitating shut down of the extraction process to clean out the settling section. Addition of Lewis base to the mixing section may reduce or eliminate the size of a rag layer or reduce its rate of formation, based upon the size and rate of formation of the rag layer in the absence of addition of Lewis base.

SUMMARY OF THE INVENTION

There are problems associated with various Lewis bases, when used to in an effort to enhance phase separation. For example, water may cause hydrolysis of water sensitive ligands, such as diphosphite or diphosphonite ligands. Ammonia forms a complex with Lewis acids, which is partially soluble in the raffinate phase of extraction process. This complex has been found to promote the cyclization reaction of adiponitrile to form 2-cyanocyclopentylidinimine, when the raffinate is subjected to distillation conditions involved in the separation of adiponitrile from the raffinate phase. Other Lewis base additives, such as pyridine, should be avoided for safety reasons. Pyridine is a teratogenic substance.

In accordance with embodiments described herein, it has been discovered that polyamines are particularly advantageous, when used as Lewis base additives. Under extraction conditions discussed herein, the polyamines tend to form a complex with Lewis acid, which is solid and readily separates into the raffinate phase. Furthermore, this solid precipitate is sufficiently dispersed in the raffinate phase to flow with the raffinate phase throughout the stages of a countercurrent multistage liquid-liquid extraction process. Although this complex does tend to catalyze the formation of 2-cyanocyclopentylidinimine from adiponitrile under certain distillation conditions, it can readily be removed from the raffinate phase from a countercurrent multistage liquid-liquid extraction process, e.g., by filtration, before the raffinate phase is subjected to such distillation conditions. It has further been found that bis-hexamethylene triamine is a particularly useful Lewis base additive in processes described herein.

The process of the present invention recovers adiponitrile from a mixture comprising adiponitrile (ADN), 3-pentenenitrile (3PN), a Lewis acid and a catalyst. The process comprises steps (a) to (j).

In step (a), a countercurrent multistage extraction zone is provided. The extraction zone comprises at least three mixer-settlers connected in series. In particular, the mixer-settlers are fluidly connected.

In step (b), a mixture comprising ADN, 3PN, Lewis acid and a catalyst is introduced to a first terminal mixer-settler in the series. In step (c), an extraction solvent is introduced into the second terminal mixer-settler in the series.

In step (d), a light phase comprising extraction solvent and a heavy phase comprising ADN and 3PN is formed in the settling sections of each of the mixer-settlers. In step (e), the heavy phase is caused to flow progressively from the first terminal mixer-settler through each of the intermediate mixer-settlers connected in series and into the second terminal mixer-settler. In step (f), the light phase is caused to flow progressively from the second terminal mixer-settler through each of the intermediate mixer-settlers connected in series and into the first terminal mixer-settler.

In step (g), the light phase comprising extraction solvent and extracted catalyst is withdrawn from the first terminal mixer-settler. In step (h), the heavy phase comprising ADN and 3PN is withdrawn from the second terminal mixer-settler.

In step (h), the withdrawn light phase from step (g) is distilled to separate extraction solvent from catalyst. In step (i), the withdrawn heavy phase from step (h) is distilled to separate ADN from 3PN.

The catalyst comprises zero valent nickel and a phosphorus-containing ligand, such as a bidentate phosphite ligand or a bidentate phosphonite ligand. A polyamine is added to the mixing section of the first terminal mixer-settler to form a precipitate comprising a complex of the Lewis acid with the polyamine. The precipitate is entrained in the flow of heavy phase through the series of mixer-settlers. The precipitate is withdrawn from the second terminal mixer-settler, along with the heavy phase, which comprises ADN and 3PN.

The complex of Lewis acid and polyamine formed in the mixing section of the first terminal mixer-settler may be capable of catalyzing the cyclization reaction of ADN to form 2-cyanocyclopentylideneimine (CPI). The complex may be removed from the raffinate phase prior to subjecting contents of the raffinate phase to distillation conditions involving temperatures to promote the catalyzed conversion of ADN to CPI. In particular, the ADN recovery process may comprise additional steps (k) and (l). In step (k), precipitate comprising a complex of the Lewis acid with the polyamine is removed from the heavy phase withdrawn in step (h). Step (l) takes place after (k) and prior to separating dinitriles comprising ADN from compounds having a boiling point higher than the boiling point of ADN. For example, step (l) may take place prior to separating ADN from 3PN.

The catalyst may comprise a bidentate phosphite ligand or a bidentate phosphonite ligand. The Lewis acid may comprise, for example, $ZnCl_2$ or triphenylborane.

The extraction solvent feed from the second stage of the countercurrent multistage extraction zone may comprise at least 1000 ppm, for example, from 2000 to 5000 ppm, of phosphorus-containing ligand. The extraction solvent feed from the second stage may comprise at least 10 ppm, for example, from 20 to 200 ppm, of nickel. At least one stage of the extraction may be carried out above 40° C.

The feed mixture to the countercurrent multistage extraction zone may be an effluent stream from a hydrocyanation process. The hydrocyanation process may include a 3-pentenenitrile hydrocyanation process or a 1,3-butadiene hydrocyanation process.

Examples of polyamines, which may be added to the mixing section of the first terminal mixer-settler, include hexamethylene diamine, bis-hexamethylene triamine and 1,2-diaminocyclohexane. For example, bis-hexamethylene triamine may be added to the mixing section of the first terminal mixer-settler.

When the phosphorus-containing ligand is a diphosphonite-containing ligand, the diphosphonite ligand may have the formula L:

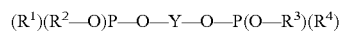

$$(R^1)(R^2—O)P—O—Y—O—P(O—R^3)(R^4) \qquad L$$

where $R^1$ and $R^2$ are each independently identical or different, separate or bridged organic radicals; $R^3$ and $R^4$ are each independently identical or different, separate or bridged organic radicals; and Y is a bridging group.

Examples of phosphonite-containing compounds of formula (L) may be diphosphonite ligands of formula (LI) or (formula LII):

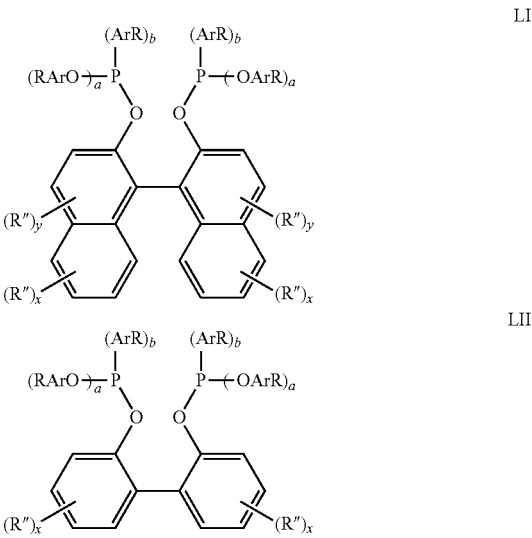

wherein:
x=0 to 4;
y=0 to 2;
a and b individually are either 0, 1, or 2, provided a+b=2;
each Ar is individually phenyl or naphthyl, and the two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide;
each R is individually hydrogen, ethenyl, propenyl, acryloyl, methacryloyl, an organic radical with a terminal ethenyl, propenyl, acryloyl, or methacryloyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;
each Ar can be further substituted with linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;

each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether.

Examples of diphosphonite ligands of formula (LII) include compounds where at least one R represents ethenyl, propenyl, acryloyl, methacryloyl or the organic radical with a terminal ethenyl, propenyl, acryloyl, or methacryloyl group or at least one R" represents ethenyl, propenyl, or the organic radical with a terminal ethenyl or propenyl group.

An example of a diphosphonite ligand of formula (LII) is a compound of formula (IV):

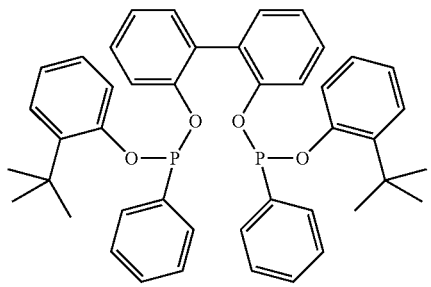

IV

Diphosphonite ligands and the synthesis of these diphosphonite ligands are described in U.S. Pat. No. 6,924,345 and in U.S. Pat. No. 7,935,229.

When the phosphorus-containing ligand is a diphosphite-containing ligand, the ligand may have the formula of diphosphite-containing ligands described in International Patent Publication No. WO 2013/095853. Particular examples of diphosphite ligands are described hereinafter with reference to ligands of formulae I to XX.

DETAILED DESCRIPTION OF THE INVENTION

The processes of the present invention involve methods for recovering phosphorus-containing ligand from a mixture comprising phosphorus-containing ligand and organic dinitriles, using liquid-liquid extraction.

Figure 1:
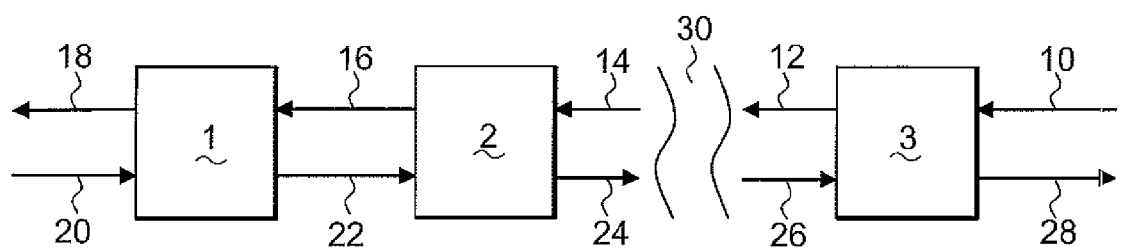
FIG. 1 is a diagram showing the flow of fluids through a multistage countercurrent liquid-liquid extractor.

FIG. 1 is a diagram of a multistage countercurrent liquid-liquid extractor. Lines in FIG. 1 represent flow of materials, rather than any particular type of equipment, such as pipes.

Three stages are depicted in FIG. 1. The first stage is depicted by mixer-settler 1. The second stage is depicted by mixer-settler 2. The final stage is depicted by mixer-settler 3. Gap 30 represents a space where additional stages may be inserted. For example, one or more, for example, from one to four, mixer-settlers may be inserted in gap 30 between mixer-settler 2 and mixer-settler 3.

In FIG. 1, mixer-settler 1 and mixer-settler 3 represent the terminal mixer-settlers of the multistage countercurrent liquid-liquid extractor. According to terminology used herein, mixer-settler 1 represents the first terminal mixer-settler, and mixer-settler 3 represents the second terminal mixer-settler. Any mixer-settler connected in series between the first terminal mixer-settler 1 and the second terminal mixer-settler 3 is referred to as an intermediate mixer-settler.

In FIG. 1, a fresh extraction solvent feed, for example, cyclohexane, is introduced into the multistage countercurrent extractor via line 10. The extraction solvent or light phase exiting from mixer-settler 3 passes through line 12 to the next stage of the multistage extractor. In a multistage countercurrent liquid-liquid extractor having three stages, extraction solvent in line 12 would pass directly into stage 2 via line 14. Extraction solvent from stage 2 passes through line 16 to stage 1. The extraction solvent comprising extracted phosphorus-containing ligand passes out of the stage 1 mixing and settling section through line 18.

A feed comprising phosphorus-containing ligand is fed into the stage 1 mixer-settler via line 20. The feed further comprises a mixture comprising organic mononitriles and dinitriles, which is immiscible with the extraction solvent. The feed further comprises a Lewis acid. In stage 1, a portion of the phosphorus-containing ligand is extracted into the extraction solvent which exits stage 1 via line 18. The immiscible dinitrile and mononitrile mixture or the heavy phase is removed from the stage 1 mixer-settler by line 22 and is passed into the stage 2 mixer-settler. A portion of the phosphorus-containing ligand is extracted into the light phase in the stage 2 mixer-settler. The heavy phase exits the stage 2 mixer-settler by line 24. Similarly, if there are additional stages in gap 30 shown in FIG. 1, extraction of phosphorus-containing ligand will take place in such intermediate stages in a similar manner to that taking place in stage 2.

After the heavy phase passes through the first stage and any intermediate stages, it passes through the final stage mixer-settler 3. In particular, the heavy phase is introduced into mixer-settler 3 through line 26. After passing through the final stage mixer-settler 3, the heavy phase exits via fine 28.

Thus, it can be seen that the multistage countercurrent liquid-liquid extractor comprises three or more stages with countercurrent flow of extraction solvent and heavy phase. In view of the direction of flow of light and heavy phase through the stages of extraction, it will be appreciated that the concentration of solute, e.g., phosphorus-containing ligand, is highest in both the light and heavy phases of the first stage and lowest in the light and heavy phases of the final stage.

Figure 2:
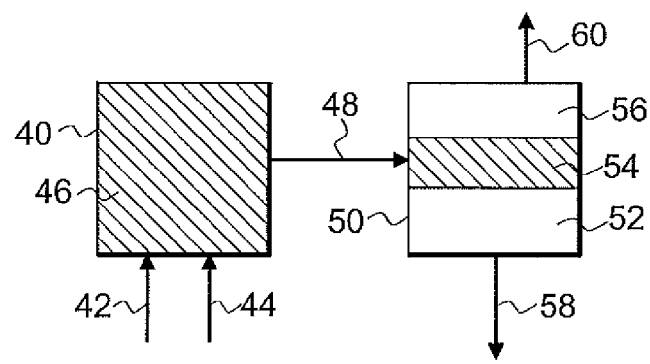
FIG. 2 is a diagram showing a mixing section and a settling section of a stage of a multistage countercurrent liquid-liquid extractor.

FIG. 2 is a diagrammatic representation of one type a mixer-settler. This mixer-settler may be used in any of the stages shown in FIG. 1. This mixer-settler comprises a mixing section 40 and a settling section 50. The mixing section 40 and the settling section 50 are separate. All of the effluent from the mixing section 40 flows into the settling section 50. Fluid from the mixing section 40 flows through the settling section 50 in a horizontal manner, although there is also no restriction of movement of fluids vertically throughout the settling section 50.

An extraction solvent is introduced into the mixing section 40 by line 42. A feed comprising phosphorus-containing ligand is introduced into the mixing section 40 by line 44. Alternatively, the contents of lines 42 and 44 may be combined upstream of the mixing section 40 and introduced into mixing section 40 through a single inlet. These two feeds are mixed in the mixing section 40 to provide a mixed phase comprising an emulsion phase represented in FIG. 2 by shaded area 46.

Line 48 represents the flow of mixed phase 46 from the mixing section 40 into the settling section 50. As depicted in FIG. 2, there are three phases in the settling section 50, including a heavy phase 52, a mixed phase 54, and a light phase 56. The heavy phase 52 is depleted in phosphorus-containing ligand, insofar as it has a lower concentration of phosphorus-containing ligand as compared with the concentration of phosphorus-containing ligand in feed 44, due to the extraction of phosphorus-containing ligand into the light phase 56. Correspondingly, the light phase 56 is enriched in phosphorus-containing ligand, insofar as it has a higher concentration of phosphorus-containing ligand as compared with the concentration of phosphorus-containing ligand in extraction solvent feed 42, due to the extraction of phosphorus-containing ligand into the light phase 56. At least a portion of the heavy phase 52 exits the settling section 50 via line 60. At least a portion of the light phase 56 is removed from the settling section 50 via line 58.

Although not shown in FIG. 2, which is diagrammatically shows the flow of fluids, it will be understood that each of the mixing section 40 and the settling section 50 may comprise one or more stages, subsections, compartments or chambers. For example, settling section 50 may include more than one chamber between the point of introduction of the mixed phase 46 through line 48 and the point of withdrawal of light phase and heavy phase through lines 58 and 60. Horizontal extension between the point of introduction of the mixed phase 46 through line 48 and the point of withdrawal of light and heavy phases through lines 58 and 60 promotes settling of the light and heavy phases 56 and 52. The size of the mixed phase 54 may become progressively smaller as fluids settle and flow through the chamber. For example, the final chamber from where fluids are removed may include little or no mixed phase 54. It will further be understood that mixing section 40 may include one or more types of mixing apparatus, such as an impeller, not shown in FIG. 2.

Figure 3:
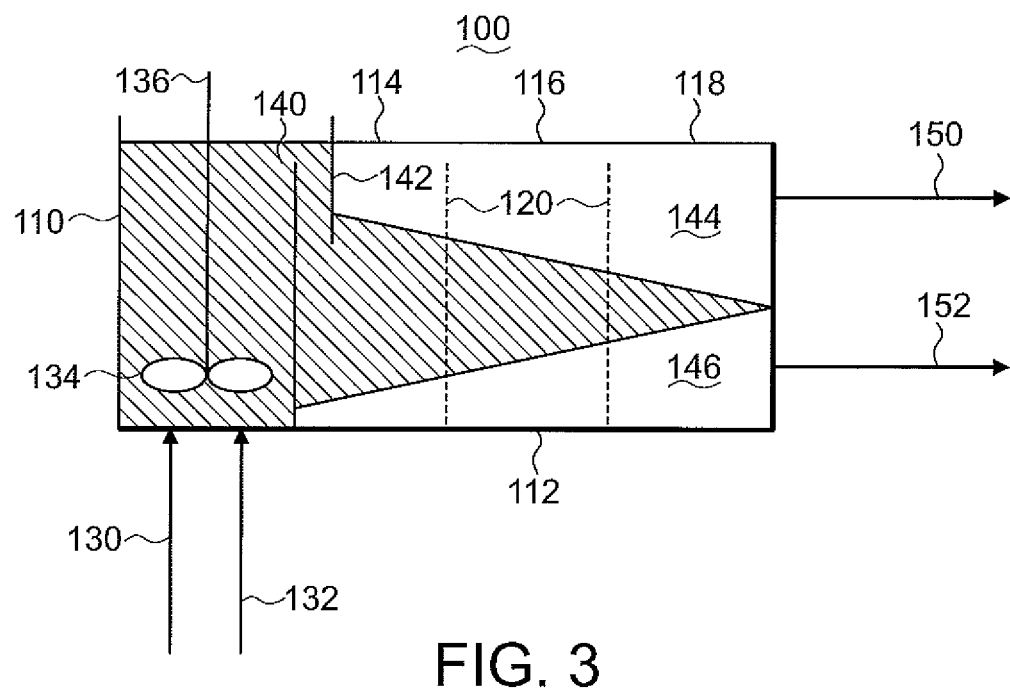
FIG. 3 is a diagram showing a mixing/settling apparatus (i.e. a mixer-settler) having three chambers in the settling section.

FIG. 3 provides a representation of a mixer-settler 100 having a multistage settling section. Mixer-settler 100 has a mixing section 110 and a settling section 112. In mixer-settler 100, the mixing section 110 is separate from the settling section 112. The settling section has three compartments, represented in FIG. 3 as sections 114, 116, and 118. These sections are separated by coalescence plates 120. The coalescence plates 120 may be designed to provide flow of separated light and heavy phases between chambers, while restricting the flow of emulsion phase between chambers. A feed comprising a phosphorus-containing ligand is passed into the mixing section 110 via line 130. The extraction solvent is introduced into mixing section 110 via line 132. The mixing section 110 includes an impeller 134 mounted on shaft 136 to provide for mechanical mixing of fluids. Mixing of the feeds provides a mixed phase comprising an emulsion phase represented in FIG. 3 by shading 140.

The mixed phase 140 flows into the settling section 112 as an overflow from the mixing section 110. This mixed phase 140 is prevented from flowing directly into the light phase 144 by baffle plate 142. As settling occurs in settling section 112, the volume of the mixed phase 140 decreases, the volume of the light phase 144 increases, and the volume of the heavy phase 146 increases. Heavy phase 146 is removed from settling section 112, in particular from chamber 118, via line 152 and light phase 144 is removed from settling section 112, in particular, from chamber 118, via line 150.

It is desirable for both a mononitrile and a dinitrile to be present in the countercurrent contactor. For a discussion of the role of monodentate and bidentate ligand in extraction of hydrocyanation reactor effluent streams, see U.S. Pat. No. 3,773,809 to Walter and U.S. Pat. No. 6,936,171 to Jackson and McKinney.

For the process disclosed herein, suitable molar ratios of mononitrile to dinitrile components include 0.01 to 2.5, for example, 0.01 to 1.5, for example 0.65 to 1.5.

Maximum temperature is limited by the volatility of the hydrocarbon solvent utilized, but recovery generally improves as the temperature is increased. Examples of suitable operating ranges are 40° C. to 100° C. and 50° C. to 80° C.

The controlled addition of monophosphite ligands may enhance settling. Examples of monophosphite ligands that may be useful as additives include those disclosed in Drinkard et al U.S. Pat. No. 3,496,215, U.S. Pat. No. 3,496,217, U.S. Pat. No. 3,496,218, U.S. Pat. No. 5,543,536, and published PCT Application WO 01/36429 (BASF).

As described herein, the addition of polyamine to a mixture comprising phosphorus-containing ligand, organic mononitriles and organic dinitriles enhances settling, especially when the mixture comprises a Lewis acid, such as $ZnCl_2$. Polyamines are organic compounds having two or more amino groups. These amino groups may be primary, secondary or tertiary amino groups. The polyamines may be aliphatic or cycloaliphatic compounds having from 1 to 15 carbon atoms. Examples of polyamines include polymethylene diamines having from 2 to 10 carbon atoms, dimers of such polymethylene diamines, and trimers of such polymethylene diamines. Particular examples of such polyamines include hexamethylene diamine, a dimer of hexamethylene diamine and a trimer of hexamethylene diamine. Bis-hexamethylene triamine (BHMT) is a dimer of hexamethylene diamine (HMD). Another example of a polyamine is a diaminocyclohexane, such as 1,2-diaminocyclohexane. The addition of polyamine tends to reduce or eliminate any inhibiting effect of Lewis acid on catalyst and ligand recovery.

The reaction product of Lewis acid with polyamine becomes entrained in the raffinate phase as it moves through the multistage countercurrent liquid-liquid extractor. In particular, this product may forms a precipitate in the raffinate phase in the form of a complex of Lewis acid with polyamine. It will be understood that the polyamine is a Lewis base. This precipitate exists as a dispersion of fine particles distributed throughout the raffinate phase. This precipitate may be removed by conventional techniques, such as filtration, centrifugation or distillation accompanied by removal of bottoms containing the precipitate, after the raffinate is removed from the last stage (i.e. the second terminal mixer-settler) of the multistage countercurrent liquid-liquid extractor.

The phosphorus-containing ligand extracted by the processes described herein may comprise bidentate phosphorus-containing ligands. These extracted ligands comprise free ligands (e.g., those which are not complexed to nickel) and those which are complexed to nickel. Accordingly, it will be understood that extraction processes described herein are useful for recovering phosphorus-containing ligand which are metal/ligand complexes, such as a complex of zero valent nickel with at least one ligand comprising a bidentate-phosphorus containing ligand.

Phosphorus-Containing Ligands

The catalysts used in the process of the invention comprise a zero-valent nickel and at least one phosphorus-containing (P-containing) ligand. The P-containing ligand may be selected from the group consisting of a phosphite, a phosphonite, a phosphinite, a phosphine, and a mixed P-containing ligand or a combination of such members.

The P-containing ligands chemically bound to nickel as complexes comprising zero-valent nickel, and the free P-containing ligands not bonded to said complexes, may be monodentate or multidentate, for example bidentate or tridentate. The term "bidentate" is well known in the art and means both phosphorus atoms of the ligand may be bonded to a single metal atom. The term "tridentate" means the three phosphorus atoms on the ligand may be bonded to a single metal atom. The terms "bidentate" and "tridentate" are also known in the art as chelate ligands.

As used herein, the term "mixed P-containing ligand" means a multidentate P-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

Diphosphite Ligands

Examples of bidentate phosphite ligands useful in the invention include those having the following structural formulae:

I

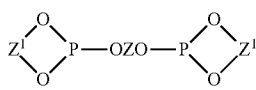

II

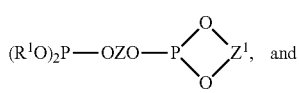

III, and wherein in I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

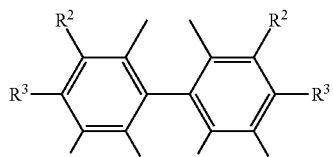

IV

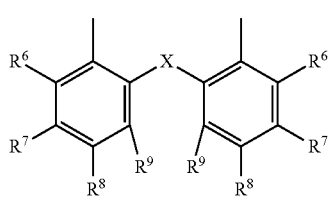

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

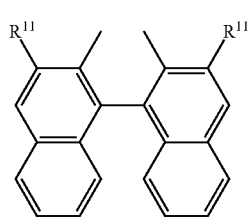

VI

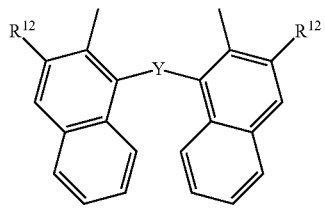

VII and wherein
$R^{11}$ and $R^{12}$ are independently selected from the group consisting of H, $C_1$ to $C_{12}$ alkyl, and $C_1$ to $C_{12}$ alkoxy; and $CO_2R^{13}$,
$R^{13}$ is $C_1$ to $C_{12}$ alkyl or $C_6$ to $C_{10}$ aryl, unsubstituted or substituted, with $C_1$ to $C_4$ alkyl;
Y is O, S, or $CH(R^{14})$;
$R^{14}$ is H or $C_1$ to $C_{12}$ alkyl;

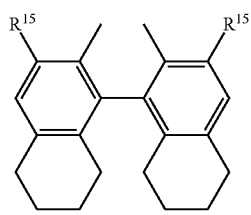

VIII wherein
$R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl, and $C_1$ to $C_{12}$ alkoxy groups may be straight chain or branched.

Another example of a formula of a bidentate phosphite ligand that is useful in the present process is that having the Formula X, shown below

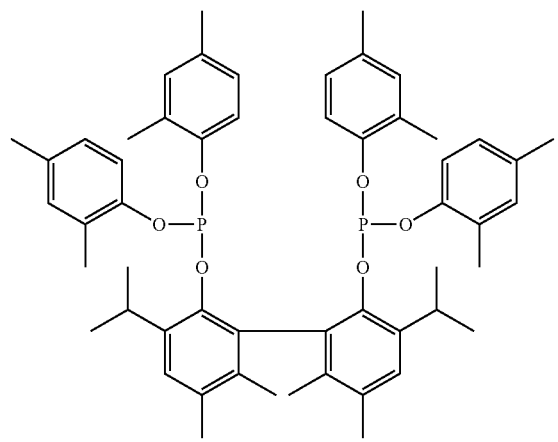

X

Further examples of bidentate phosphite ligands that are useful in the present process include those having the Formulae XI to XIV, shown below wherein for each formula, $R^{17}$ is selected from the group consisting of methyl, ethyl or iso-propyl, and $R^{18}$ and $R^{19}$ are independently selected from H or methyl:

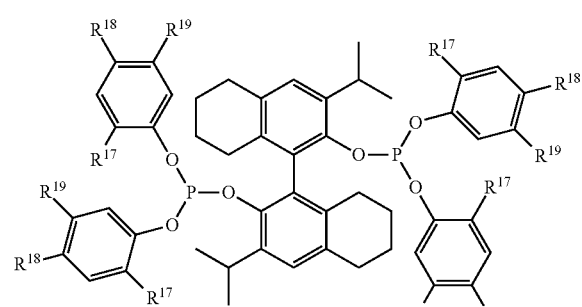

XI

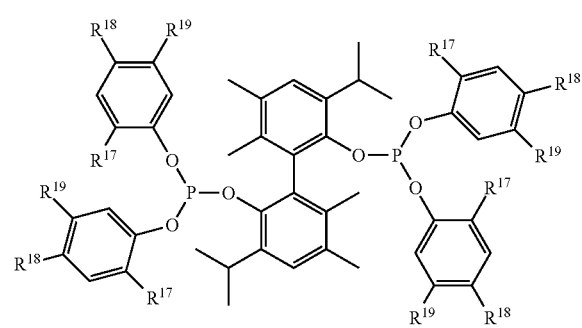

XII

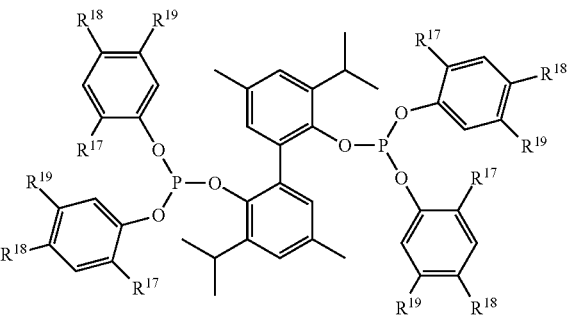

XIII

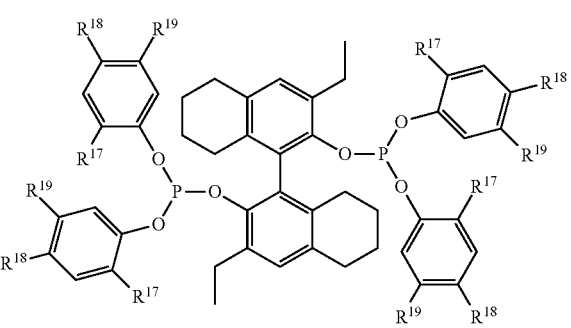

XIV

Additional examples of bidentate phosphite ligands that are useful in the present process include a ligand selected from a member of the group represented by Formulae XV and XVI, in which all like reference characters have the same meaning, except as further explicitly limited:

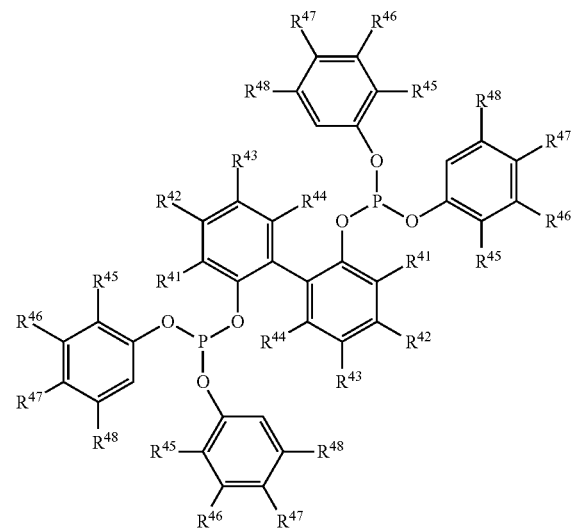

Formula XV

-continued

Formula XVI

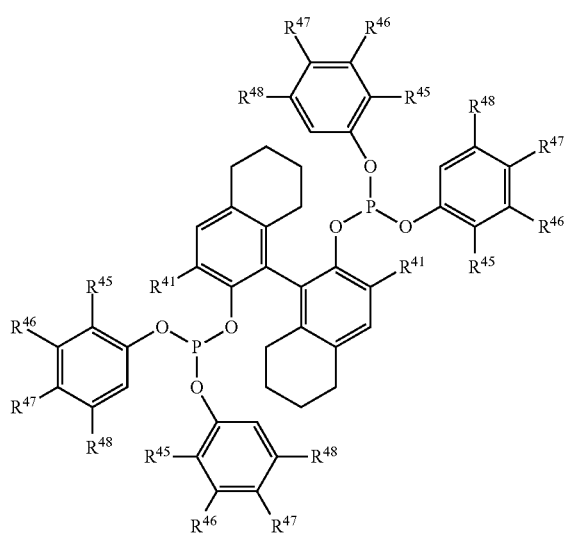

wherein
$R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

For example, the bidentate phosphite ligand can be selected from a member of the group represented by Formula XV and Formula XVI, wherein
$R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula XV, wherein
$R^{41}$, $R^{44}$, and $R^{45}$ are methyl;
$R^{46}$, $R^{47}$ and $R^{48}$ are H; and
$R^{43}$ is a $C_1$ to $C_4$ hydrocarbyl;
or
$R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;
or the bidentate phosphite ligand can be selected from a member of the group represented by Formula XVI, wherein
$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand may be represented by Formula XV, wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae X to XVI are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae X to XVI, respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom.

Further examples of bidentate phosphite ligands that are useful in the present process include those having the formula XX to LIII, shown below wherein $R^{17}$ is selected from the group consisting of methyl, ethyl or isopropyl, and $R^{18}$ and $R^{19}$ are independently selected from H or methyl:

XX

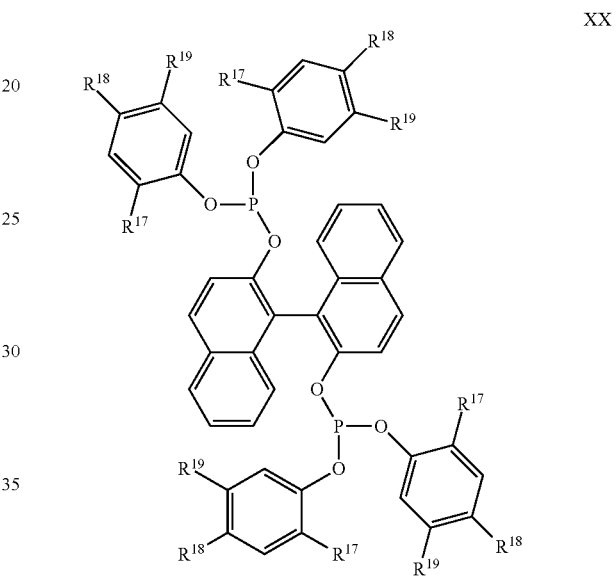

Further examples of bidentate phosphite ligands that are useful in the present process are described with reference to the formulae formula XXI to LIII in International Patent Publication No. WO 2013/095853.

Additional suitable bidentate phosphites are of the type disclosed in U.S. Pat. Nos. 5,512,695; 5,512,696; 5,663,369; 5,688,986; 5,723,641; 5,847,101; 5,959,135; 6,120,700; 6,171,996; 6,171,997; 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

Diphosphonite Ligands

The diphosphonite-containing ligand may be a diphosphonite ligand of formula (L):

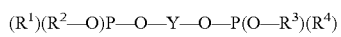

where $R^1$ and $R^2$ are each independently identical or different, separate or bridged organic radicals; $R^3$ and $R^4$ are each independently identical or different, separate or bridged organic radicals; and Y is a bridging group.

The $R^1$ and $R^2$ radicals may each independently be identical or different organic radicals. Examples of $R^1$ and $R^2$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^3$ and $R^4$ radicals may each independently be identical or different organic radicals. Examples of $R^3$ and $R^4$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^1$ and $R^2$ radicals may each be separate or bridged. The $R^3$ and $R^4$ radicals may also each be separate or bridged. The $R^1$, $R^2$, $R^3$ and $R^4$ radicals may each be separate, two may be bridged and two separate, or all four may be bridged.

Examples of phosphonite-containing ligands of formula (L) may be diphosphonite ligands of formula (LI) or (formula LII):

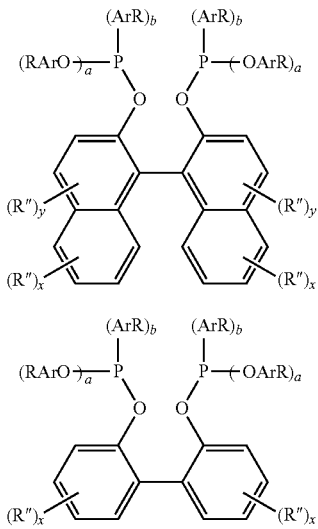

wherein:
x=0 to 4;
y=0 to 2;
a and b individually are either 0, 1, or 2, provided a+b=2;
each Ar is individually phenyl or naphthyl, and the two Ar groups that are directly or indirectly (through an oxygen) bonded to the same phosphorus atom may be linked to each other by a linking unit selected from the group consisting of direct bond, alkylidene, secondary or tertiary amine, oxygen, sulfide, sulfone, and sulfoxide;
each R is individually hydrogen, ethenyl, propenyl, acryloyl, methacryloyl, an organic radical with a terminal ethenyl, propenyl, acryloyl, or methacryloyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;
each Ar can be further substituted with linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether;
each R" is individually hydrogen, ethenyl, propenyl, an organic radical with a terminal ethenyl or propenyl group, linear or branched alkyl, cycloalkyl, acetal, ketal, aryl, alkoxy, cycloalkoxy, aryloxy, formyl, ester, fluorine, chlorine, bromine, perhaloalkyl, hydrocarbylsulfinyl, hydrocarbylsulfonyl, hydrocarbylcarbonyl or cyclic ether.

At least one R in formula (LI) or formula (LII) may represent ethenyl, propenyl, acryloyl, methacryloyl or the organic radical with a terminal ethenyl, propenyl, acryloyl, or methacryloyl group and/or at least one R" may represent ethenyl, propenyl, or the organic radical with a terminal ethenyl or propenyl group.

An example of a diphosphonite ligand of formula (LII) is a compound of formula (LIII):

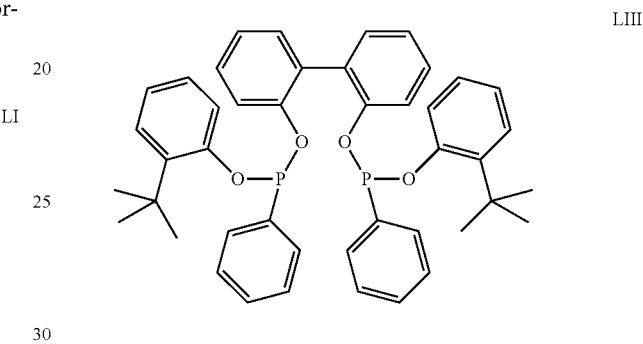

Diphosphonite ligands and the synthesis of these diphosphonite ligands are described in U.S. Pat. No. 6,924,345 and in U.S. Pat. No. 7,935,229.

Extraction Solvent

Suitable hydrocarbon extraction solvents include paraffins and cycloparaffins (aliphatic and alicyclic hydrocarbons) having a boiling point in the range of about 30° C. to about 135° C., including n-pentane, n-hexane, n-heptane and n-octane, as well as the corresponding branched chain paraffinic hydrocarbons having a boiling point within the range specified. Useful alicyclic hydrocarbons include cyclopentane, cyclohexane and cycloheptane, as well as alkyl substituted alicyclic hydrocarbons having a boiling point within the specified range. Mixtures of hydrocarbons may also be used, such as, for example, mixtures of the hydrocarbons noted above or commercial heptane which contains a number of hydrocarbons in addition to n-heptane. Cyclohexane is the preferred extraction solvent.

Recovery of Products

The lighter (hydrocarbon) phase recovered from the multistage countercurrent liquid-liquid extractor is directed to suitable equipment to recover catalyst, reactants, etc. for recycle to the hydrocyanation, while the heavier (lower) phase containing dinitriles recovered from the multistage countercurrent liquid-liquid extractor is directed to product recovery after removal of any solids, which may accumulate in the heavier phase. These solids may contain valuable components which may also be recovered, e.g., by the process set forth in U.S. Pat. No. 4,082,811.

The solids in the heavier phase, also referred to herein as the raffinate phase, comprise a complex of Lewis acid and polyamine in the form of dispersion of fine particles. The raffinate phase may also comprise extraction solvent, such as cyclohexane, pentenenitriles, which comprise 3-pentenenitrile, compounds with a higher boiling point than adiponitrile and compounds with a boiling point greater than the boiling point of pentenenitriles and less than the boiling point of adiponitrile. The complex of Lewis acid and polyamine may be removed from the raffinate phase prior to removing extraction solvent, and especially before removing pentenenitriles from the raffinate phase.

The complex of Lewis acid and polyamine may be removed by any customary solids removal process. Examples of such processes include filtration, crossflow filtration, centrifugation, sedimentation, classification and decantation. Common apparatus for such solids removal include filters, centrifuges and decanters.

It has been found that the complex of Lewis acid and polyamine may catalyze the unwanted cyclization reaction of adiponitrile to form 2-cyanocyclopentylideneimine (CPI), especially when the raffinate phase is heated to temperatures used in the $K_3$ column, discussed hereinafter, which is used to separate dinitriles, which comprise adiponitrile, from compounds having a boiling point higher than adiponitrile.

Figure 4:
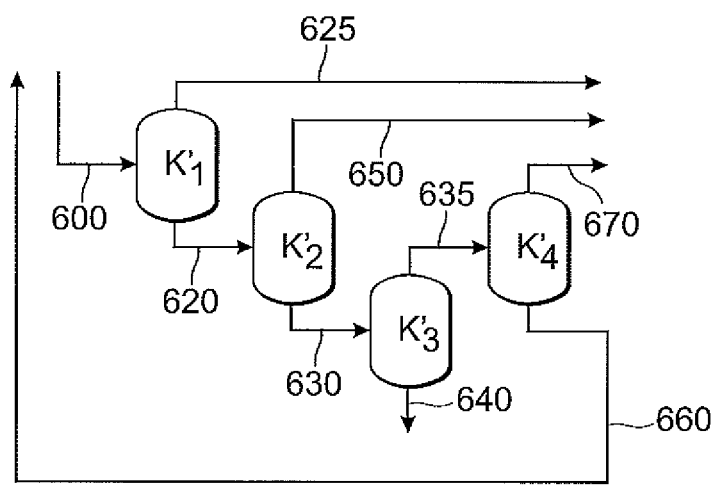
FIG. 4 is a diagram showing a distillation train which may be used to recover adiponitrile from a raffinate stream.

FIG. 4 shows a distillation train, which may be used as an adiponitrile purification section. FIG. 4 of the present application corresponds to FIG. 3 of United States Patent Application Publication No. 2013/0211126. Line 600 transports a raffinate stream from an extraction zone into distillation column $K'_1$, where extraction solvent is separated from higher boiling components of the raffinate stream. In particular, extraction solvent, such as cyclohexane, is withdrawn from distillation column $K'_1$ through line 625, and higher boiling components of the raffinate stream are withdrawn from distillation column through line 620.

The solvent-depleted strewn in line 620 is then passed into distillation column $K'_2$, where pentenenitrile is separated from higher boiling components remaining in the raffinate stream. In particular, pentenenitrile, such as 3PN and any 2M3BN present, is withdrawn from distillation column $K'_2$ through line 650, and higher boiling components of the raffinate stream are withdrawn from distillation column $K'_2$ through line 630.

The pentenenitrile-depleted stream in line 630 is then passed into distillation column $K'_3$, where dinitriles are separated from higher boiling components remaining in the raffinate stream. In particular, dinitriles, such as ADN and MGN, are withdrawn from distillation column $K'_3$ through line 635, and higher boiling components of the raffinate stream are withdrawn from distillation column $K'_3$ through line 640. These higher boiling components in line 640 may comprise, for example, catalyst degradation products.

The dinitrile-enriched stream in line 635 is then passed into distillation column $K'_4$, where adiponitrile is separated from lower boiling dinitriles, such as MGN. In particular, MGN is withdrawn from distillation column $K'_4$ through line 670, and a purified adiponitrile stream is withdrawn from distillation column $K'_4$ through line 660.

Although not shown in FIG. 4, a complex of Lewis acid and Lewis base in the form of a dispersed solid precipitate may be removed, e.g., by filtration, from the raffinate before the stream is introduced into distillation column $K'_1$. According to another embodiment, this complex may be removed from the stream in line 620 before this stream enters distillation column $K'_2$. According to another embodiment, this complex may be removed from the stream in line 630 before this stream enters distillation column $K'_3$.

EXAMPLES

In the following examples, values for extraction coefficient are the ratio of weight fraction of catalyst in the extract phase (hydrocarbon phase) versus the weight fraction of catalyst in the raffinate phase (organonitrile phase). An increase in extraction coefficient results in greater efficiency in recovering catalyst. As used herein, the terms, light phase, extract phase and hydrocarbon phase, are synonymous. Also, as used herein, the terms, heavy phase, organonitrile phase and raffinate phase, are synonymous.

Analyses of the extract and the raffinate streams of the catalyst extraction were conducted on an Agilent 1100 series HPLC and via ICP. The HPLC was used to determine the extraction efficiency of the process.

In the Examples which follow, a diphosphite ligand is present. However, it is believed that the results of these Examples would be essentially the same if a different phosphorus-containing ligand, such as a diphosphonite ligand, was substituted for the diphosphite ligand.

Example 1

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. This extract from the second stage comprised approximately 50 ppm nickel and 3100 ppm diphosphite ligand. The hexamethylene diamine concentration in the system was 0 ppm.

The reactor product was approximately:
85% by weight $C_6$ dinitriles
14% by weight $C_5$ mononitriles
1% by weight catalyst components
200 ppm by weight active nickel
230 ppm by weight zinc.

The laboratory reactor was then mixed at 500 rotations-per-minute, for 10 minutes, and then allowed to settle for 1 minute. After settling for 1 minute, a stable emulsion was present throughout the extract phase. Samples were obtained of the extract and raffinate phases of the extractor and analyzed to determine the extent of catalyst extraction. The ratio of active nickel present in the extract phase vs. the raffinate phase was found to be 5. The concentration of zinc in the raffinate was found to be 230 ppm.

Example 2

Example 1 was repeated except that hexamethylene diamine (HMD) was added to the system. In particular, a sufficient amount of HMD was added so that the molar ratio of Zn/HMD was 12 in the system.

Example 3

Example 1 was repeated except that hexamethylene diamine (HMD) was added to the system. In particular, a sufficient amount of HMD was added so that the molar ratio of Zn/HMD was 6 in the system.

Example 4

Example 1 was repeated except that hexamethylene diamine (HMD) was added to the system. In particular, a sufficient amount of HMD was added so that the molar ratio of Zn/HMD was 2.4 in the system.

Example 5

Example 1 was repeated except that hexamethylene diamine (HMD) was added to the system. In particular, a sufficient amount of HMD was added so that the molar ratio of Zn/HMD was 1.2 in the system.

Example 6

Example 1 was repeated except that bis-hexamethylene triamine (BHMT) was added to the system. In particular, a sufficient amount of BHMT was added so that the molar ratio of Zn/BMHT was 5.9 in the system.

Example 7

Example 1 was repeated except that bis-hexamethylene triamine (BHMT) was added to the system. In particular, a sufficient amount of BHMT was added so that the molar ratio of Zn/BMHT was 2.9 in the system.

Example 8

Example 1 was repeated except that bis-hexamethylene triamine (BHMT) was added to the system. In particular, a sufficient amount of BHMT was added so that the molar ratio of Zn/BMHT was 1.2 in the system.

Example 9

Example 1 was repeated except that bis-hexamethylene triamine (BHMT) was added to the system. In particular, a sufficient amount of BHMT was added so that the molar ratio of Zn/BMHT was 12 in the system.

Example 10

Example 1 was repeated except that 1,2-diaminocyclohexane (DCH) was added to the system. In particular, a sufficient amount of DCH was added so that the molar ratio of Zn/DCH was 1.6 in the system.

Example 11

Example 1 was repeated except that 1,2-diaminocyclohexane (DCH) was added to the system. In particular, a sufficient amount of DCH was added so that the molar ratio of Zn/DCH was 2 in the system.

Example 12

Example 1 was repeated except that 1,2-diaminocyclohexane (DCH) was added to the system. In particular, a sufficient amount of DCH was added so that the molar ratio of Zn/DCH was 4 in the system.

Example 13

Example 1 was repeated except that 1,2-diaminocyclohexane (DCH) was added to the system. In particular, a sufficient amount of DCH was added so that the molar ratio of Zn/DCH was 8 in the system.

Example 14

Example 1 was repeated except that triethylamine (TEA) was added to the system. In particular, a sufficient amount of TEA was added so that the molar ratio of Zn/TEA was 1 in the system.

Example 15

Example 1 was repeated except that octylamine was added to the system. In particular, a sufficient amount of TEA was added so that the molar ratio of Zn/octylamine was 1.3 in the system.

Comparative Example 16

Example 1 was repeated except that polyethyleneglycol (PEG-600) was added to the system. In particular, a sufficient amount of PEG-600 was added so that the molar ratio of Zn/PEG-600 was 1.5 in the system.

Comparative Example 17

Example 1 was repeated except that adipamide was added to the system. In particular, a sufficient amount of adipamide was added so that the molar ratio of Zn/adipamide was 2.3 in the system.

Comparative Example 18

Example 1 was repeated except that triphenyl phosphine ($Ph_3P$) was added to the system. In particular, a sufficient amount of $Ph_3P$ was added so that the molar ratio of $Zn/Ph_3P$ was 1 in the system.

Example 19

Example 1 was repeated except that calcium hydroxide ($Ca(OH)_2$) was added to the system. In particular, a sufficient amount of $Ca(OH)_2$ was added so that the molar ratio of $Zn/Ca(OH)_2$ was 0.3 in the system.

Results of Examples 1-19 are summarized in Table 1.

TABLE 1

| Ex./CEx. | Temp (° C.) | Time (min) | Zn/Additive | Additive | KLL | Zn/Ni |
| --- | --- | --- | --- | --- | --- | --- |
| 1 | 65 | 10 |  | None | 5 | 1.15 |
| 2 | 65 | 10 | 12.0 | HMD | 13 | 1.09 |
| 3 | 65 | 10 | 6.0 | HMD | 13 | 1.11 |
| 4 | 65 | 10 | 2.4 | HMD | 23 | 0.43 |
| 5 | 65 | 10 | 1.2 | HMD | 84 | 0.12 |
| 6 | 65 | 10 | 5.9 | BHMT | 102 | 0.12 |
| 7 | 65 | 10 | 2.9 | BHMT | 80 | 0.17 |
| 8 | 65 | 10 | 1.2 | BHMT | 112 | 0.17 |
| 9 | 65 | 10 | 12.0 | BHMT | 18 |  |
| 10 | 65 | 10 | 1.6 | DCH | 119 | 0.85 |
| 11 | 65 | 10 | 2 | DCH | 114 |  |
| 12 | 65 | 10 | 4 | DCH | 27 | 1.03 |
| 13 | 65 | 10 | 8 | DCH | 8 | 1.05 |
| 14 | 65 | 10 | 1 | TEA | 20 | 0.94 |
| 15 | 65 | 10 | 1.3 | Octylamine | 63 | 0.96 |
| 16 | 65 | 10 | 1.5 | PEG-600 | 5 | 1.07 |
| 17 | 65 | 10 | 2.3 | Adipamide | 6 |  |
| 18 | 65 | 10 | 1 | $Ph_3P$ | 4 | 1.15 |
| 19 | 65 | 10 | 0.3 | $Ca(OH)_2$ | 14 |  |

KLL = amount of catalyst in the extract/amount of catalyst in the raffinate;
Zn/Additive = the molar ratio of the zinc-to-additive during extraction;
Zn/Ni = the ratio of the total amount of zinc-to-nickel remaining in both phases after the extraction, as determined by inductively coupled plasma spectrometry (ICP).

The data summarized in Table 1 represent evaluations of a number of materials as potential additives for improved catalyst extraction. Examples 1-5 show the beneficial effect of hexamethylene diamine (HMD) on catalyst extraction, as the HMD loading increases (represented by decreasing Zn/Additive ratio) the catalyst extraction efficiency (represented by KLL) increases. Examples 6-9 show the beneficial effect of bis-hexamethylene triamine (BHMT) on catalyst extraction. Examples 10-13 show the beneficial effect of 1,2-diaminocyclohexane (DCH) on catalyst extraction. Example 15 shows the beneficial effect of adding octylamine on catalyst extraction. Example 19 shows the beneficial effect of calcium hydroxide on catalyst extraction. By way of contrast, Comparative Examples 16-18 show little effect on catalyst extraction using PEG-600, adipamide, and triphenyl phosphine, respectively.

The results in Table 1 show that BHMT produced superior results. For example, as compared with HMD, at a Zn/Additive ratio of 1.2, BHMT produced a greater KLL value than HMD. As compared with DCH, BHMT produced a greater KLL value and a smaller Zn/Ni ratio, when used at a Zn/Additive ratio of 5.9, than DCH, when used at a Zn/Additive ratio of 4. As compared with octylamine, BHMT produced a greater KLL value and a smaller Zn/Ni ratio, when used at a Zn/Additive ratio of 1.2, than octylamine, when used at a Zn/Additive ratio of 1.3.

Examples 20-25

These Examples 20-25 illustrate that effective catalyst recovery occurs for a mononitrile to dinitrile ratio greater than 0.65.

Five different mixtures comprised of a Ni diphosphite complex, with the diphosphite ligand shown in Structure XX (where $R^{17}$ is isopropyl, $R^{18}$ is H, and $R^{19}$ is methyl), $ZnCl_2$ (equimolar with Ni) and differing in the ratio of mononitrile to dinitrile, were separately liquid-liquid batch extracted with an equal weight of cyane (i.e. cyclohexane). The molar ratio of organic mononitrile to organic dinitrile and the resulting extraction coefficients are shown in the Table 2 below. A compound may be effectively recovered if it has an extraction coefficient of 1 or greater at solvent to feed ratios greater than 1 using a countercurrent multistage extractor.

TABLE 2

Catalyst and ligand extraction coefficients for varying ratios of mononitriles-to-dinitriles

| Example | mononitrile/ dinitrile | Catalyst extraction coefficient | Ligand extraction coefficient |
|---|---|---|---|
| 20 | 2.33 | 1.28 | 4.09 |
| 21 | 1.85 | 1.33 | 8.08 |
| 23 | 1.19 | 2.02 | 16.97 |
| 24 | 0.91 | 2.63 | 35.99 |
| 25 | 0.57 | 4.82 | 49.59 |

Example 26

This Example demonstrates the effect of hold-up time on the extractability of the diphosphite ligand catalyst.

A mixture comprised predominantly of organic dinitriles and a Ni diphosphite complex, the structure of the diphosphite ligand being shown in Structure XX (where $R^{17}$ is isopropyl, $R^{18}$ is H, and $R^{19}$ is methyl) and $ZnCl_2$ (equimolar with Ni) was divided into two portions. Both portions are liquid-liquid extracted in a three-stage contactor at 40° C., with an equal weight of cyclohexane. Both portions were sampled with time and the progress of the catalyst recovery into the extract phase is shown in Table 3 as the percent of the final steady state value achieved at a given time.

TABLE 3

Concentration of Diphosphite ligand with time in the extracting solvent phase.

| Time, minutes | % of steady state concentration at 40° C. |
|---|---|
| 2 | 12 |
| 4 | 19 |
| 8 | 34 |
| 14 | 52 |
| 30 | 78 |
| 60 | 100 |
| 91 | 100 |

Example 27

This Example illustrates the effect of temperature on the extractability of catalyst with first-stage extraction solvent recycle.

A mixture comprised predominantly of organic dinitriles and a Ni diphosphite complex, the structure of the diphosphite ligand being shown in Structure XXIV (where $R^{17}$ is methyl, $R^{18}$ is methyl and $R^{19}$ is H) and $ZnCl_2$ (equimolar with Ni) was divided into three portions. The portions were batch liquid-liquid extracted at 50° C., 65° C. and 80° C., respectively, with an equal weight of n-octane and monitored with time. The results are shown in Table 4.

TABLE 4

| Time | % of steady state at 50° C. | % of steady state at 65° C. | % of steady state at 80° C. |
|---|---|---|---|
| 2 | 0.0 | 0.0 | 1.8 |
| 4 | 0.0 | 0.0 | 1.6 |
| 8 | 0.0 | 0.0 | 3.6 |
| 14 | 0.0 | 0.0 | 4.3 |
| 20 | 0.0 | 0.0 | 3.6 |
| 30 | 0.0 | 0.0 | 7.6 |
| 60 | 0.0 | 1.6 | 16.3 |
| 90 | 0.7 | 4.0 | 48.6 |

Example 28

This Example demonstrates the effect of adding water in three-stage extraction with cyclohexane recycle in the last stage.

Fifteen grams of a mixture comprised predominantly of organic dinitriles and a Ni diphosphite complex, the structure of the diphosphite ligand being shown in Structure XXIV (where $R^{17}$ is methyl, $R^{18}$ is methyl and $R^{19}$ is H) and $ZnCl_2$ (equimolar with Ni), was extracted in a three-stage continuous extractor at a temperature of 50° C. with an equal weight of cyclohexane for one hour resulting in an catalyst extraction coefficient of 4.3, as measured by the amount of catalyst in the extract of the first stage divided by the amount of catalyst in the feed of the reaction mixture fed to the last stage of the three-stage countercurrent extractor.

To this mixture, 100 microliters of water was added. After continuing to heat and agitate for another hour, the diphosphite Ni extraction coefficient was measured as 13.4—a threefold increase.

Examples 29 and 30

These Examples demonstrate the effect of adding hexamethylene diamine (HMD) to the extraction zone.

Example 1 was repeated except that hexamethylene diamine was added to the product of a pentene-hydrocyanation reaction. To a 50 mL, jacketed, glass laboratory extractor, equipped with a magnetic stirbar, digital stir-plate, and maintained at 65° C., was charged 10 grams of the product of pentene-hydrocyanation reactor product, and 10 grams of the extract from the second stage of a mixer-settler cascade, operated in counter-current flow.

The reactor product was approximately:
85% by weight $C_6$ dinitriles
14% by weight $C_5$ mononitriles
1% by weight catalyst components
360 ppm by weight active nickel.

The laboratory reactor was then mixed at 1160 rotations-per-minute, for 20 minutes, and then allowed to settle for 15 minutes. A stable emulsion was present throughout the extract phase in the absence of the addition of HMD. After 15 minutes of settling, essentially no emulsion phase was present when HMD was added. Samples were obtained of the extract and raffinate phases of the extractor and analyzed to determine the extent of catalyst extraction.

TABLE 5

Effect of hexamethylene diamine on catalyst extraction

| Example | Concentration of HMD added (ppm) | Catalyst recovery (KLL) | Stable emulsion |
|---|---|---|---|
| 1 | 0 | 14 | Yes |
| 29 | 250 | 43 | No |
| 30 | 500 | 80 | No |

Examples 31-36

These Examples demonstrate the beneficial effect of adding hexamethylene diamine (HMD) on the reaction temperature required for catalyst extraction. For Examples 31-33, Example 1 was repeated, but the mixing time was 20 minutes, and the temperature was varied as indicated in Table 6. For Examples 34-36, Example 5 was repeated, and the temperature was varied as indicated in Table 6.

TABLE 6

Effect of hexamethylene diamine on temperature for catalyst extraction.

| Example | Temp (° C.) | KLL | Zn/HMD |
|---|---|---|---|
| 31 | 65 | 16.76 | No HMD |
| 32 | 55 | 13.25 | No HMD |
| 33 | 45 | 8.06 | No HMD |
| 34 | 65 | 84.42 | 1.2 |
| 35 | 55 | 82.91 | 1.2 |
| 36 | 45 | 82.00 | 1.2 |

The data summarized in Table 6 represent evaluations of catalyst extraction performed at varying temperature from 45 to 65 degrees Celsius, with and without HMD present. Examples 31-33 show that catalyst extraction increases linearly with increasing temperature (represented by KLL). Examples 34-36 show that catalyst extraction does not require increased temperature when HMD is added.

Examples 37-44

These Examples demonstrate the beneficial effect of adding hexamethylene diamine (HMD) on the mixing time required for catalyst extraction. For Examples 37-40, Example 31 was repeated, and the mixing time was varied as indicated in Table 7. For Examples 41-44, Example 5 was repeated, and the mixing time was varied as indicated in Table 7.

TABLE 7

Effect of hexamethylene diamine on mixing time required for catalyst extraction.

| Example | Mixing Time | KLL | Zn/HMD |
|---|---|---|---|
| 37 | 20 | 16.13 | No HMD |
| 38 | 10 | 14.86 | No HMD |
| 39 | 5 | 14.49 | No HMD |
| 40 | 1 | 11.05 | No HMD |
| 41 | 10 | 84.42 | 1.2 |
| 42 | 5 | 114.34 | 1.2 |
| 43 | 1 | 98.24 | 1.2 |
| 44 | 0.5 | 56.23 | 1.2 |

The data summarized in Table 7 represent evaluations of catalyst extraction performed at varying mixing time from 20 minutes to 30 seconds, with and without HMD present. Examples 37-40 show that a decrease in catalyst extraction occurs when the mixing time is decreased to less than 5 minutes. Examples 41-44 show that catalyst extraction does not decrease until the mixing time is decreased to less than 1 minute, when HMD added.

Examples 45-48

These Examples demonstrate the beneficial effect of adding hexamethylene diamine (HMD) and bis-hexamethylene triamine (BHMT) to the mixing section of a mixer-settler, rather than to the feed line to this mixing section. Results are shown in Table 8.

TABLE 8

Effect of additive addition point.

| Example | Addition Point | Additive | Mixing Time | KLL | Stable Emulsion |
|---|---|---|---|---|---|
| 45 | Mixer | HMD | 20 | 23 | No |
| 46 | Mixer | BHMT | 20 | 80 | No |
| 47 | Feed Line | HMD | N/A | 14 | Yes |
| 48 | Feed Line | BHMT | N/A | 14 | Yes |

Examples 45-48 show that addition of the additives HMD or BHMT directly to the mixer system of a catalyst extraction system causes a beneficial increase in catalyst recovery, as indicated by increased KLL.

Examples 49-53

These Examples demonstrate the ability of complex of zinc chloride ($ZnCl_2$) and bis-hexamethylene triamine (BHMT) to catalyze the cyclization of adiponitrile (ADN) to 2-cyanocyclopentylideneimine (CPI) under conditions encountered when a raffinate stream is refined to produce purified ADN.

A simulated raffinate composition which was obtained from the tails stream of a column for removal of pentenenitriles from dinitriles (i.e. column K'$_2$ and stream 630 in FIG. 4) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 9.

TABLE 9

Amount of additive.

| Example | Additive | Amount of BHMT | Zn/BHMT |
|---|---|---|---|
| 49 | BHMT + ZnCl$_2$ | 1 wt % | 1 |
| 50 | BHMT + ZnCl$_2$ | 2 wt % | 0.5 |
| 51 | BHMT + ZnCl$_2$ | 0.5 wt % | 2 |
| 52 | BHMT | 2 wt % | N/A |
| 53 | ZnCl$_2$ | 0 | N/A |

In Table 9, it will be understood that the amount of BHMT is based on the total weight of the raffinate composition before addition of the additive. It will be further understood that the ratio of Zn/BHMT is expressed in terms of equivalents of Zn per mole of BHMT. The amount of ZnCl$_2$ added as per Example 53 (EX 53) was 3 wt %, based on the total weight of the raffinate composition before addition of the ZnCl$_2$.

After the addition of the additive, samples of the mixture were taken at 1 hour, 2 hours, 3 hours and 5 hours. These samples were analyzed, and the concentration of CPI in the samples was determined in terms of CPI (mol/L), i.e. moles of CPI per liter of the mixture. Results are shown in FIG. 5.

Figure 5:
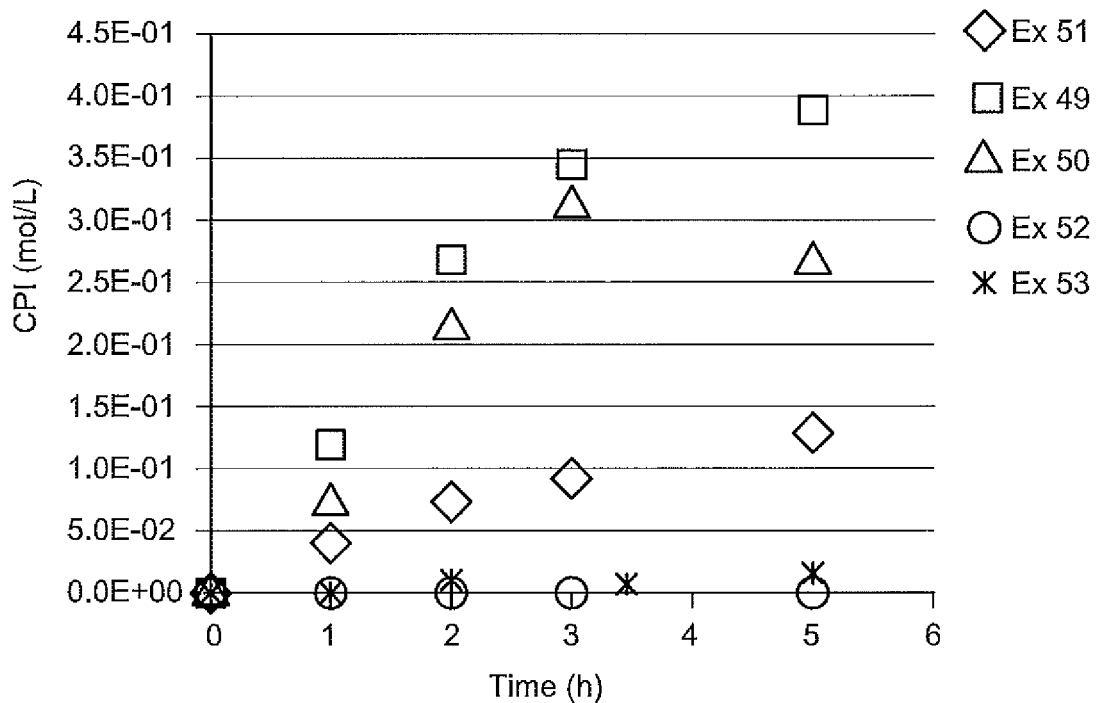
FIGS. 5 and 6 are graphs showing the conversion of adiponitrile to 2-cyanocyclopentylideneimine (CPI) in the presence of various additives over time.

FIG. 5 shows that CPI formation was negligible according to Example 52 (EX 52), wherein the additive included BHMT in the absence of ZnCl$_2$. FIG. 5 also shows that CPI formation was negligible according to Example 53 (EX 53), wherein the additive included ZnCl$_2$ in the absence of BHMT. However, FIG. 5 shows that considerable amounts of 2-cyanocyclopentylideneimine (CPI) were formed according to Examples 49-51 (EX 49 to EX 51) in increasing quantities over time when the additive included both BHMT and ZnCl$_2$.

Examples 54-56

These Examples demonstrate the ability of a complex of zinc chloride (ZnCl$_2$) and hexamethylene diamine (HMD) to catalyze the cyclization of adiponitrile (ADN) to 2-cyanocyclopentylideneimine (CPI) under conditions encountered when a raffinate stream is refined to produce purified ADN.

A raffinate material which was obtained from the tails stream of a column for removal of pentenenitriles from dinitriles (i.e. column K'$_2$ and stream 630 in FIG. 3) was used for the following examples. This raffinate had the following composition: 94% adiponitrile, 4% methylglutaronitrile, 0.1% pentenenitriles, 0.5% ethylsuccinonitrile, and 271 ppm zinc. To simulate conditions in a distillation column to distill dinitriles the raffinate was heated to 180° C.

Various additives were then added to the heated mixture. The composition of these additives is shown in Table 10.

TABLE 10

Amount of additive.

| Example | Additive | Amount of HMD | Zn/HMD |
|---|---|---|---|
| 54 | HMD + ZnCl$_2$ | 0.5 wt % | 1 |
| 55 | ZnCl$_2$ | 0 | N/A |
| 56 | HMD | 0.5 wt % | N/A |

In Table 10 it will be understood that the amount of HMD is based on the total weight of the raffinate composition before addition of the additive. It will be further understood that the ratio of Zn/HMD is expressed in terms of equivalents of Zn per mole of HMD. The amount of ZnCl$_2$ added as per Example 55 (EX 55) was 0.6 wt %, based on the total weight of the raffinate composition before addition of the ZnCl$_2$.

After the addition of the additive, samples of the mixture were taken at various times including 1 hour, 2 hours, 3 hours, 3.5 hours and 5 hours. These samples were analyzed, and the concentration of CPI in the samples was determined in terms of CPI (mol/L), i.e. moles of CPI per liter of the mixture. Results are shown in FIG. 6.

Figure 6:
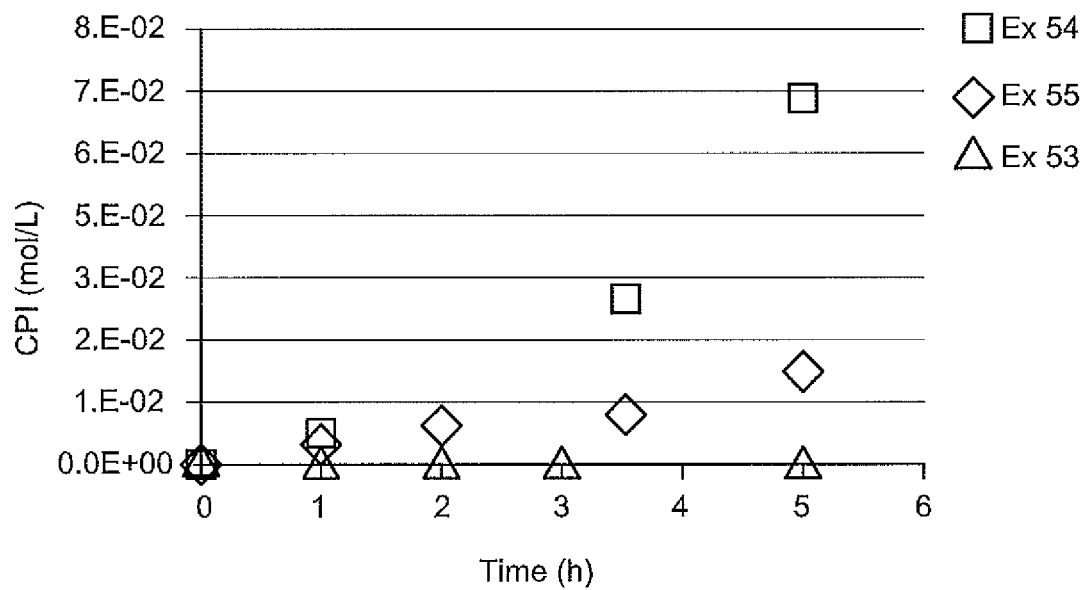

FIG. 6 shows that CPI formation was negligible according to Example 56 (EX 56), wherein the additive included HMD in the absence of ZnCl$_2$. FIG. 6 also shows that only small amounts of CPI were formed according to Example 55 (EX 55), wherein the additive included ZnCl$_2$ in the absence of HMD. However, FIG. 6 shows that considerable amounts of 2-cyanocyclopentylideneimine (CPI) were formed according to Example 54 (EX 54) in increasing quantities over time when the additive included both HMD and ZnCl$_2$, especially when the mixture was heated for 3.5 and 5 hours.

What is claimed is:

1. A process for recovering a catalyst and adiponitrile (ADN) from a mixture comprising adiponitrile, 3-pentenenitrile (3PN), a Lewis acid and a catalyst, said process comprising the steps of:
    (a) providing a countercurrent multistage extraction zone comprising at least three mixer-settlers connected in series;
    (b) introducing said mixture comprising ADN, 3PN, Lewis acid and a catalyst to a first terminal mixer-settler in the series;
    (c) introducing an extraction solvent into the second terminal mixer-settler in the series;
    (d) forming a light phase comprising extraction solvent and a heavy phase comprising ADN and 3PN in the settling sections of each of the mixer-settlers;
    (e) flowing the heavy phase progressively from the first terminal mixer-settler through each of the mixer-settlers and into the second terminal mixer-settler;
    (f) flowing the light phase progressively from the second terminal mixer-settler through each of the mixer-settlers and into the first terminal mixer-settler;
    (g) withdrawing the light phase comprising extraction solvent and extracted catalyst from the first terminal mixer-settler;
    (h) withdrawing the heavy phase comprising ADN and 3PN from the second terminal mixer-settler;
    (i) distilling the withdrawn light phase from step (g) to separate extraction solvent from catalyst; and
    (j) distilling the withdrawn heavy phase from step (h) to separate ADN from 3PN,
    wherein the catalyst comprises zero valent nickel and a phosphorus-containing ligand,
    wherein a polyamine is added to the mixing section of the first terminal mixer-settler to form a precipitate comprising a complex of the Lewis acid with the polyamine,
    wherein the precipitate is dispersed in the heavy phase in the settling section of the first mixer-settler,
    wherein the precipitate is entrained in the flow of heavy phase through the series of mixer-settlers, and
    wherein the precipitate is withdrawn from the second terminal mixer-settler, along with the heavy phase.

2. The process of claim 1, wherein the complex of Lewis acid and polyamine formed in the mixing section of the first terminal mixer-settler is capable of catalyzing the cyclization reaction of ADN to form 2-cyanocyclopentylideneimine (CPI).

3. The process of claim 1, further comprising the steps of:
(k) removing precipitate comprising a complex of the Lewis acid with the polyamine from the heavy phase withdrawn in step (h), followed by
(l) separating ADN from 3PN.

4. The process of claim 1, wherein the catalyst comprises a bidentate phosphite ligand or a bidentate phosphonite ligand.

5. The process of claim 1, wherein the Lewis acid is $ZnCl_2$.

6. The process of claim 1, wherein the catalyst comprises a diphosphite ligand of the formula:

   I

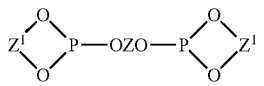   II

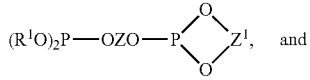   III wherein in I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and wherein Z and $Z^1$ are independently selected from the group consisting of structural formulae IV, V, VI, VII, and VIII:

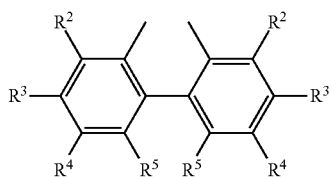   IV

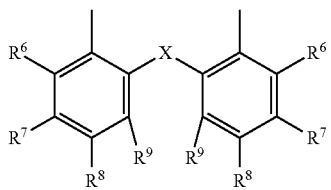   V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

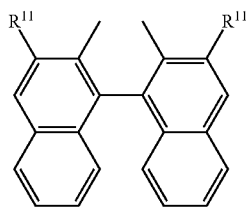   VI

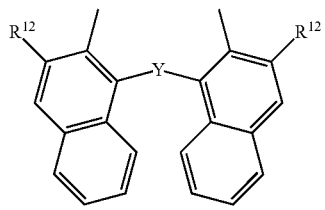   VII and wherein
$R^{11}$ and $R^{12}$ are independently selected from the group consisting of H, $C_1$ to $C_{12}$ alkyl, and $C_1$ to $C_{12}$ alkoxy and $CO_2R^{13}$,
$R^{13}$ is $C_1$ to $C_{12}$ alkyl, or $C_6$ to $C_{10}$ aryl unsubstituted or substituted with $C_1$ to $C_4$ alkyl;
Y is O, S, or $CH(R^{14})$;
$R^{14}$ is H or $C_1$ to $C_{12}$ alkyl;

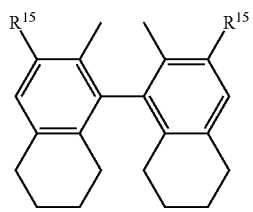   VIII wherein
$R^{15}$ is selected from the group consisting of H, $C_1$ to $C_{12}$ alkyl, and $C_1$ to $C_{12}$ alkoxy and $CO_2R^{16}$,
$R^{16}$ is $C_1$ to $C_{12}$ alkyl, or $C_6$ to $C_{10}$ aryl, unsubstituted or substituted with $C_1$ to $C_4$ alkyl,
and wherein
for structural formulae I through VIII, the $C_1$ to $C_{12}$ alkyl, and $C_1$ to $C_{12}$ alkoxy groups may be straight chain or branched.

7. The process of claim 1, wherein the catalyst comprises a diphosphonite ligand of the formula:

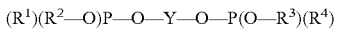   L where $R^1$ and $R^2$ are each independently identical or different, separate or bridged organic radicals; $R^3$ and $R^4$ are each independently identical or different, separate or bridged organic radicals; and Y is a bridging group.

8. The process of claim 1, wherein the extraction solvent feed from the second stage comprises at least 1000 ppm of diphosphite-containing ligand or diphosphonite-containing ligand.

9. The process of claim 1, wherein at least one stage of the extraction is carried out above 40° C.

10. The process of claim 1, wherein the extraction solvent is cyclohexane.

11. The process of claim 1 wherein the feed mixture is an effluent stream from a hydrocyanation process.

12. The process of claim 11 wherein the hydrocyanation process includes a 3-pentenenitrile hydrocyanation process.

13. The process of claim 11 wherein the hydrocyanation process includes a 1,3-butadiene hydrocyanation process.

14. The process of claim 1, wherein the polyamine is selected from the group consisting of hexamethylene diamine, bis-hexamethylene triamine and 1,2-diaminocyclohexane.

15. The process of claim 1, wherein bis-hexamethylene triamine is added to the mixing section of the first terminal mixer-settler.

\* \* \* \* \*